United States Patent
MacLeod (10) Patent No.: US 9,381,107 B2
(45) Date of Patent: Jul. 5, 2016

(54) POST SHOULDER SURGERY REHABILITATION BED WEDGE

(71) Applicant: Scott MacLeod, McLean, VA (US)

(72) Inventor: Scott MacLeod, McLean, VA (US)

( * ) Notice: Subject to any disclaimer, the term of this patent is extended or adjusted under 35 U.S.C. 154(b) by 0 days.

(21) Appl. No.: 13/650,581

(22) Filed: Oct. 12, 2012

(65) Prior Publication Data

US 2014/0101852 A1 Apr. 17, 2014

(51) Int. Cl.
 *A61F 5/37* (2006.01)
 *A61G 7/075* (2006.01)

(52) U.S. Cl.
 CPC .............. *A61F 5/3769* (2013.01); *A61G 7/075* (2013.01); *A61G 2200/327* (2013.01); *A61G 2210/10* (2013.01)

(58) Field of Classification Search
 CPC ..... A61G 13/12; A61G 13/1235; A61G 7/07; A61G 7/05715; A61G 7/075; A47C 20/023
 USPC .......... 5/644, 654, 655.3, 630, 632, 646, 621, 5/623, 655, 731, 733; D6/601
 See application file for complete search history.

(56) References Cited

U.S. PATENT DOCUMENTS

| | | | | |
|---|---|---|---|---|
| 211,741 A * | 1/1879 | Johnson | | 5/630 |
| 3,378,861 A * | 4/1968 | Lousberg | | 5/733 |
| 4,142,263 A * | 3/1979 | Pierson | | 5/660 |
| 4,270,235 A * | 6/1981 | Gutmann | | 5/646 |
| 4,853,993 A * | 8/1989 | Walpin et al. | | 5/634 |
| 5,170,522 A * | 12/1992 | Walker | | 5/615 |
| 5,311,625 A * | 5/1994 | Barker et al. | | 5/615 |
| 5,528,783 A * | 6/1996 | Kunz et al. | | 5/634 |
| 5,970,545 A * | 10/1999 | Garman et al. | | 5/615 |
| 6,009,873 A * | 1/2000 | Neviaser | | 128/845 |
| 6,021,535 A * | 2/2000 | Baus et al. | | 5/632 |
| 6,848,137 B1 * | 2/2005 | Barnes | | 5/710 |
| 6,925,670 B2 * | 8/2005 | Torrez | | 5/731 |
| 6,951,038 B1 * | 10/2005 | Ganoe, Sr. | | 5/644 |
| 7,127,759 B2 * | 10/2006 | Koops | | 5/644 |
| 7,310,840 B2 * | 12/2007 | Rubio | | 5/636 |
| 7,415,743 B2 * | 8/2008 | Rubio | | 5/722 |
| 7,681,266 B2 * | 3/2010 | Gerlach | | 5/655 |
| 8,590,848 B1 * | 11/2013 | Newlen | | 248/118 |
| 2006/0123549 A1 * | 6/2006 | Chaffee | | 5/655.3 |
| 2009/0222991 A1 * | 9/2009 | Davis, III | | 5/644 |
| 2010/0121236 A1 * | 5/2010 | Goumas | | 602/4 |
| 2010/0146708 A1 * | 6/2010 | Sakata et al. | | 5/655.3 |
| 2011/0252568 A1 * | 10/2011 | Ramp | | 5/655.3 |

* cited by examiner

*Primary Examiner* — Robert G Santos
*Assistant Examiner* — Myles Throop
(74) *Attorney, Agent, or Firm* — Usha Koshy (57) ABSTRACT

A post shoulder surgery rehabilitation apparatus in the form of a bed wedge having a shoulder support wedge structure attachment to provide the optimal support and comfort to a patient while resting or sleeping on a bed or similar structure. An exemplary embodiment of the bed wedge apparatus is capable of being inflated and deflated to the optimal angle for comfort and support for the repaired shoulder by means of a remote control switch by the patients themselves without assistance from a caregiver. Alternate embodiments of the bed wedge apparatus include ones without the need for inflation or deflation and ones that have shoulder support wedge structures for both shoulders after surgery.

2 Claims, 12 Drawing Sheets

POST SHOULDER SURGERY REHABILITATION BED WEDGE

FIELD OF THE INVENTION

The present invention is generally related to post surgical support systems and devices. More particularly, the invention is related to a bed wedge apparatus specifically configured for use by a post shoulder surgery patient to assist in the recovery and rehabilitation of the shoulder after surgery.

BACKGROUND OF THE INVENTION

Historically, recovery and rehabilitation from shoulder surgery required a lengthy stay in the hospital. More recently, there is an increasing trend towards performing shoulder and other related surgeries on an out-patient basis as a means to contain cost and increase the availability of hospital beds to patients undergoing more radical and invasive surgeries that require comprehensive post surgical aftercare. Consequently, shoulder surgeries are often done on an outpatient or same day surgery basis and the patient is sent home to manage on their own rather than being in the comfort, care and coverage of a hospital and nursing staff.

Among the most significant challenges facing a patient who has undergone shoulder surgery is finding a means to comfortably lie down on a bed for resting or sleeping without exacerbating the pain and discomfort from the surgery. This generally requires that the patient not lie in a fully supine position and keep the post surgical shoulder on a comfortable surface at a certain angle relative to the patient's body. The standard pillows used on a bed are not capable of providing the special ergonomic support required for a post surgical shoulder, nor are they a safe alternative because their use to support a post surgical shoulder may in fact exacerbate the pain and discomfort in the shoulder and prolong the rehabilitation process. Pillows need to be positioned but then shift, settle and move throughout the night making such support difficult and short lived. What is needed is a specially constructed bed accessory or device that can be placed on the bed to provide support and comfort to the post surgical shoulder while the patient is resting or sleeping on the bed. Moreover, such specially constructed bed accessory needs to support not just the shoulder on its own but when it is in a post surgical shoulder sling provided by a hospital and/or orthopedic surgeon, post surgery. Prior art in the area of bed accessories and devices have not adequately nor fully addressed the critical issues faced by a post shoulder surgery patient in providing the best support and comfort to the patient when resting or sleeping on a bed.

The use of special pillows to support the various parts of the body while resting or sleeping in bed, are well known in the art as for example, the adjustable wedge described in U.S. Pat. No. 7,089,615 to Parimuha. Some prior art have also addressed the issue of alleviating pain in the shoulders by providing specially configured pillows such as the orthopedic pillow with a recessed area to insert the shoulder while a person is lying on their side as described in U.S. Pat. No. 8,069,515 to Tingey. U.S. Pat. No. 8,043,241 to Goumas describes a support system for a post shoulder surgery patient comprising an arm cradle, side bolster and a support pillow all separately secured to a mat positioned on a bed, floor or other flat surface. A drawback with this prior art is that the patient is restricted to lying in a supine position and does not have the ability nor the means to raise his upper body when they feel the need to, as for instance, to assist in getting out of bed, having a drink from a cup or bottle, or having a meal while still resting on the bed. Nor does such prior art have a hinge mechanism to ensure the stable and even elevation and recline of the patient. Also, such prior art is not designed to support a patient using a shoulder sling provided by a hospital or orthopedic surgeon and as such likely explains the lack of adoption of the prior art into the commercial post surgical medical market. Finally, the prior art does not stabilize the shoulder in a position of abduction (i.e. positioned resting against the chest of the patient) and/or external rotation (i.e. positioned out at an angle away from the body) as is required by medical protocol for a number of common shoulder surgeries and conditions.

Inflatable mattresses and pillows that facilitate the raising of the upper body are also known in the art. U.S. Pat. Appl. Pub. No. 2007/0028388 (Fletcher) describes an inflatable mattress-like apparatus to lift a person from a supine position on the ground to a sitting position above ground level. U.S. Pat. No. D651,840 and U.S. Pat. No. 7,992,241 both to Davis III describe an inflatable, wedge-shaped upper body elevator device suitable for lounging. U.S. Des. Pat. No. 407, 259 to Jackson illustrates an inflatable orthopedic pillow. None of these devices are suitable or safe for use by a patient who is attempting to recuperate from shoulder surgery. Among the many drawbacks of these and other inflatable mattresses, pillows and wedge-shaped devices are their narrow and flimsy construction with no peripheral support for resting the repaired shoulder at a comfortable angle to alleviate the post operative pain and discomfort, nor barriers on either side of the devices to prevent the patient from rolling off a bed accidentally while resting or sleeping. None of them are also capable of being remotely inflated by the patient's themselves to a comfortable angle to rest their post surgery shoulder.

The present invention addresses and overcomes the deficiencies in the prior art for an apparatus or device specifically constructed for the comfort and rehabilitation of a post shoulder surgery patient while lying, resting, or sleeping on a bed or similar structure. The features and advantages of the bed wedge of the present invention are configured to provide support, comfort and rehabilitation of the repaired shoulder on its own as well as for use and support of the shoulder while in a hospital and/or orthopedic surgeon-prescribed shoulder sling. The present invention will be best understood through the summary of the invention, detailed description of the drawings and the claims that follow.

SUMMARY OF THE INVENTION

The present invention is a bed wedge specifically configured for use by a post shoulder surgery patient while resting or sleeping on a bed.

The primary object of the present invention is to provide a post shoulder surgery bed wedge device that has a specially configured means to support the injured shoulder both when it is in a post surgical shoulder sling or out of the sling.

A second object of the present invention is to provide a device that is capable of maintaining the post surgical shoulder at the optimal angle of comfort and support while the patient is resting or sleeping on the bed.

A third object of the invention is to provide a device that can be remotely inflated or deflated by the patient without assistance from others while resting on the device.

A fourth object of the present invention is to provide a device that maintains the post surgical shoulder at a constant angle during the elevation and deflation of the device using the remote control switch.

A fifth object of the present invention to provide a post shoulder surgery device that inflates and deflates evenly to avoid stress on the surgically repaired shoulder.

A sixth object of the present invention is to provide a device that is light weight, portable, and can when needed, be securely placed on the surface of a bed for use by a patient recovering from shoulder surgery. The device should also be sufficiently wide and sturdy to prevent it from dislocation due to the movement of the patient while reposing on the device on top of a bed.

In an exemplary embodiment of the present invention, the bed wedge device has a mattress surface made of Urethane® or other comparable material supported on a solid frame constructed from plastic or other light weight material, with a shoulder support wedge also made of Urethane® or other comparable material configured on one side of the mattress, and a detachable pillow positioned on the top end of the mattress to support the head. In this embodiment, the solid frame has inflation tubing attached to one of its sides and connected to an electromechanical inflation device plugged into a wall outlet. In this embodiment, there is also a remote control switch easily accessible by the patient with their unencumbered hand to turn on the electromechanical inflation device to inflate the bed wedge, through an inflatable inner core, to the optimal angle of comfort and support of the shoulder both while in and outside of a shoulder sling. In this embodiment of the bed wedge, the patient on their own without the aid of a nurse or caregiver is able to inflate and deflate the device from a lying position to a fully seated position or vice versa.

In an alternate embodiment of the bed wedge of the present invention, the device is constructed to work without the need to inflate it. In this embodiment, the device is pre-configured with the appropriate slant and angle that provides the maximum comfort and support to the post surgery shoulder when it is placed in the shoulder support wedge.

In yet another embodiment of the bed wedge of the present invention, the device is configured with two shoulder support wedges one on either side of the top mattress surface structure in the event that both shoulders have undergone surgery and need the required support for their rehabilitation.

In this summary describing the objects and embodiments of the present invention and in the specification in general, references to the "exemplary embodiment," "alternate embodiment," "another embodiment" or "yet another embodiment" do not necessarily all refer to the same embodiment(s). Rather, the references to the various embodiments mean that a particular feature, structure, or characteristics described in conjunction with a specific embodiment is included in at least some embodiments, but not necessarily all embodiments of the invention. The objects, embodiments and features of the post shoulder surgery bed wedge of the present invention as described in this summary of the invention will be further appreciated and will become obvious to one skilled in the art when viewed in conjunction with the drawings, detailed description of the invention and the appended claims.

DETAILED DESCRIPTION OF THE INVENTION

Figure 1:
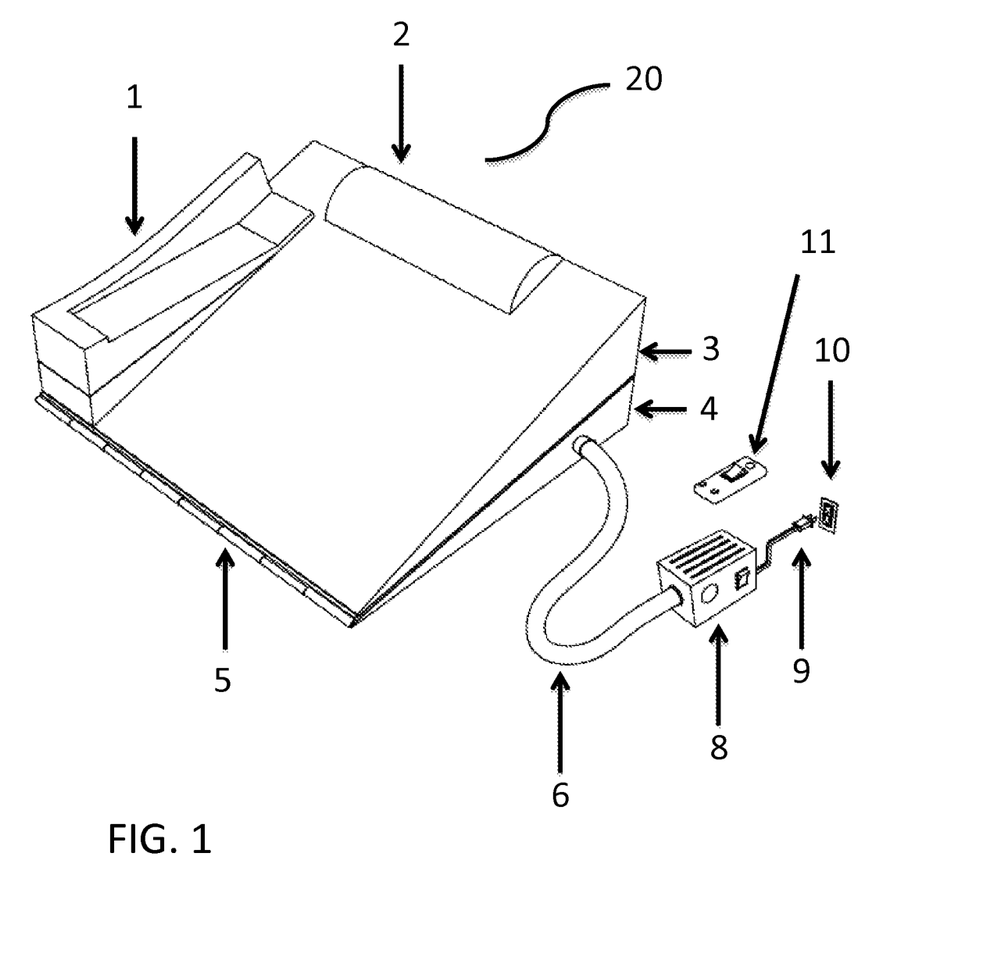
FIG. 1 is a perspective view of an exemplary embodiment of the present invention.

Referring now to the drawings, in which like numbers represent like elements in the several views, and in particular to FIG. 1 an exemplary embodiment of the bed wedge 20 of the present invention is shown. The bed wedge 20 has a shoulder support wedge structure 1 placed on one side of the bed wedge 20. The shoulder support wedge structure 1 is ergonomically configured to provide support to a shoulder that has undergone surgery which may be in a postsurgical shoulder sling or one that is outside the sling. The bed wedge 20 has a specially adapted pillow 2 to cradle the head of the patient reclining on the bed wedge 20 when resting or sleeping. The bed wedge 20 has a triangular wedge-shaped mattress 3 supported on a sturdy and solid triangular wedge-shaped frame 4 with their broad and narrow ends aligned to form a slope. The narrow ends of the mattress 3 and the narrow end of the solid frame 4 are connected by means of a hinge 5 which helps to hold the mattress 3 and solid frame 4 together at these ends when the bed wedge 20 is inflated by means of an electromechanical inflation device 8 connected to the solid frame 4 of the bed wedge 20 through an inflation tubing 6. The electromechanical inflation device 8 is plugged into a wall outlet 10 through a two or three pronged cable 9. A remote control switch 11 is configured to be within easy reach of the patient with their unencumbered hand to inflate and deflate the bed wedge 20 to a sufficient incline and angle that provides the maximum support and optimal comfort to the repaired shoulder while the patient is resting or sleeping on the bed.

Figure 2:
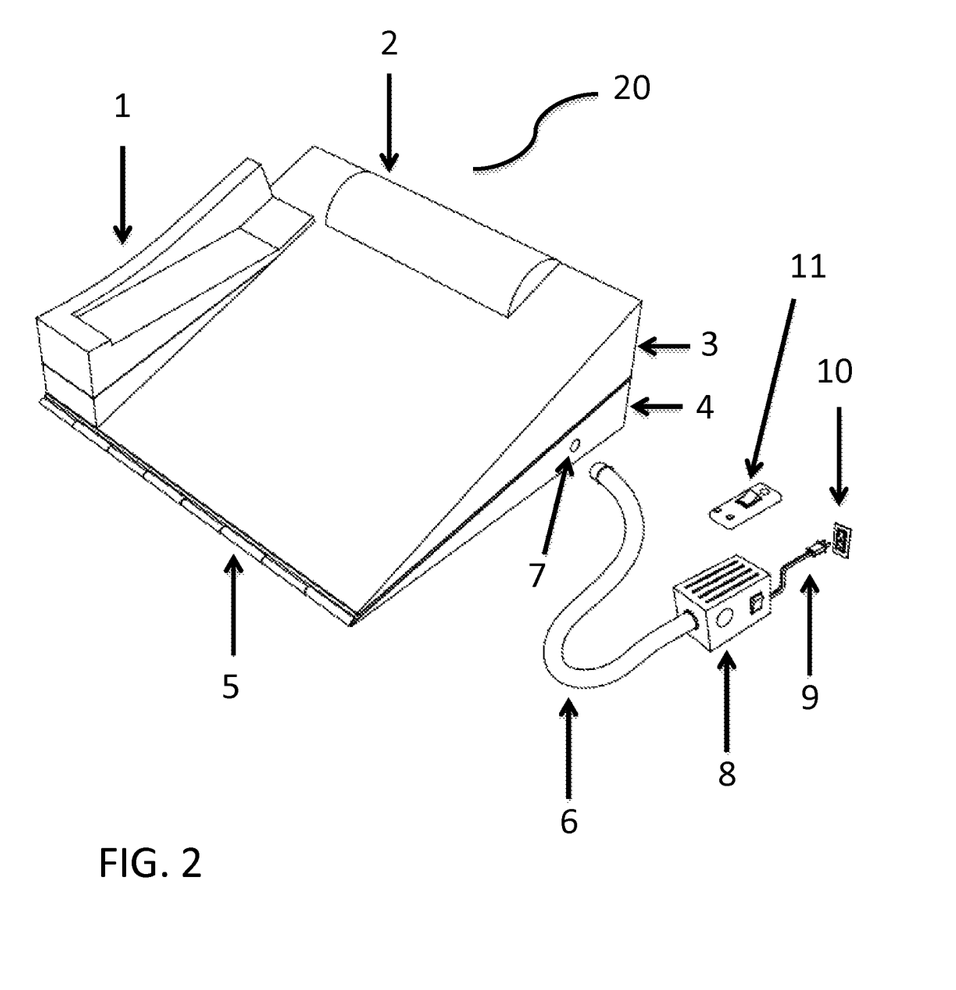
FIG. 2 is another perspective view of the exemplary embodiment of the present invention.

Referring now to FIG. 2 another perspective view of the exemplary embodiment of the bed wedge 20 is shown with the inflation tubing 6 detached from the solid frame 4 exposing the orifice 7 in the solid frame 4 through which the inflation tubing 6 is threaded and held in place to inflate the bed wedge 20.

Figure 3:
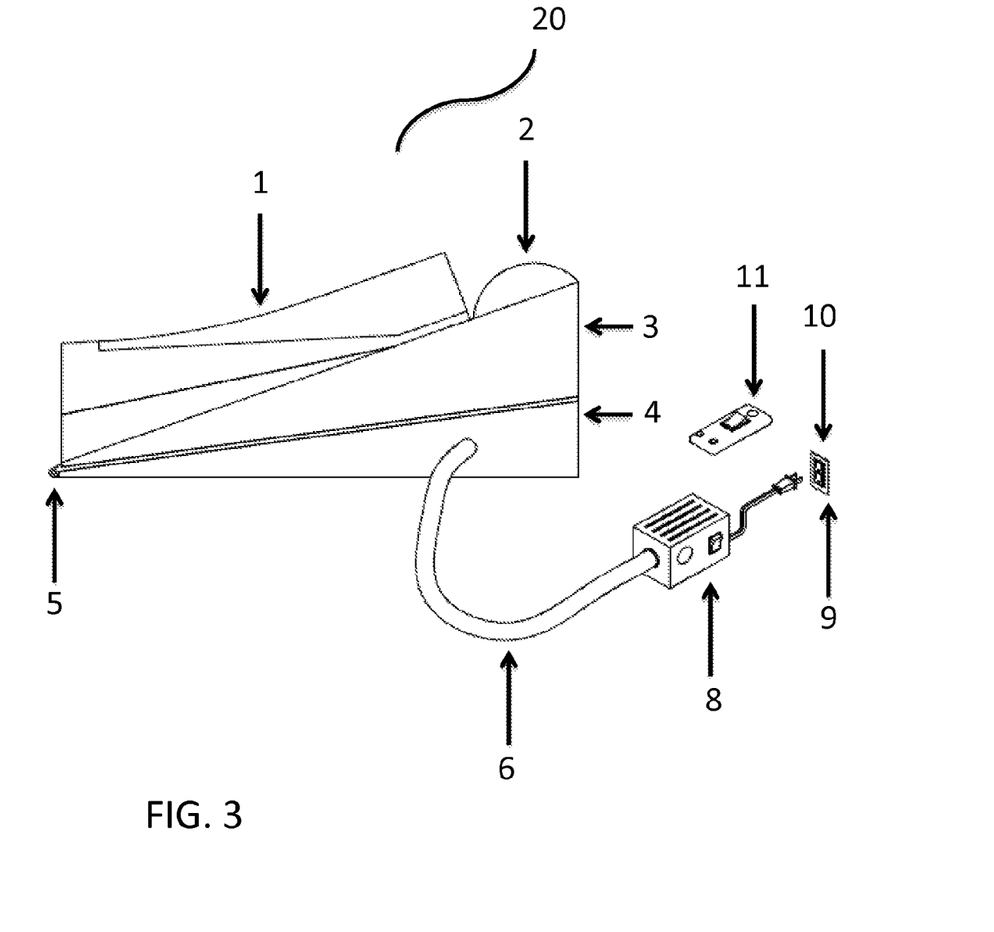
FIG. 3 is a side view of an exemplary embodiment of the present invention.

FIG. 3 is a side view of the exemplary embodiment of the bed wedge 20 of the present invention providing a perspective of the slant in the structure with the shoulder support wedge structure 1 seen rising over the mattress 3 structure held up by the solid frame 4 structure held together at their narrow ends by the hinge 5. The inflation tubing 6 is seen exiting the solid frame 4 and is connected to the electromechanical inflation device 8 plugged into the wall outlet 10 through the cable 9.

Figure 4:
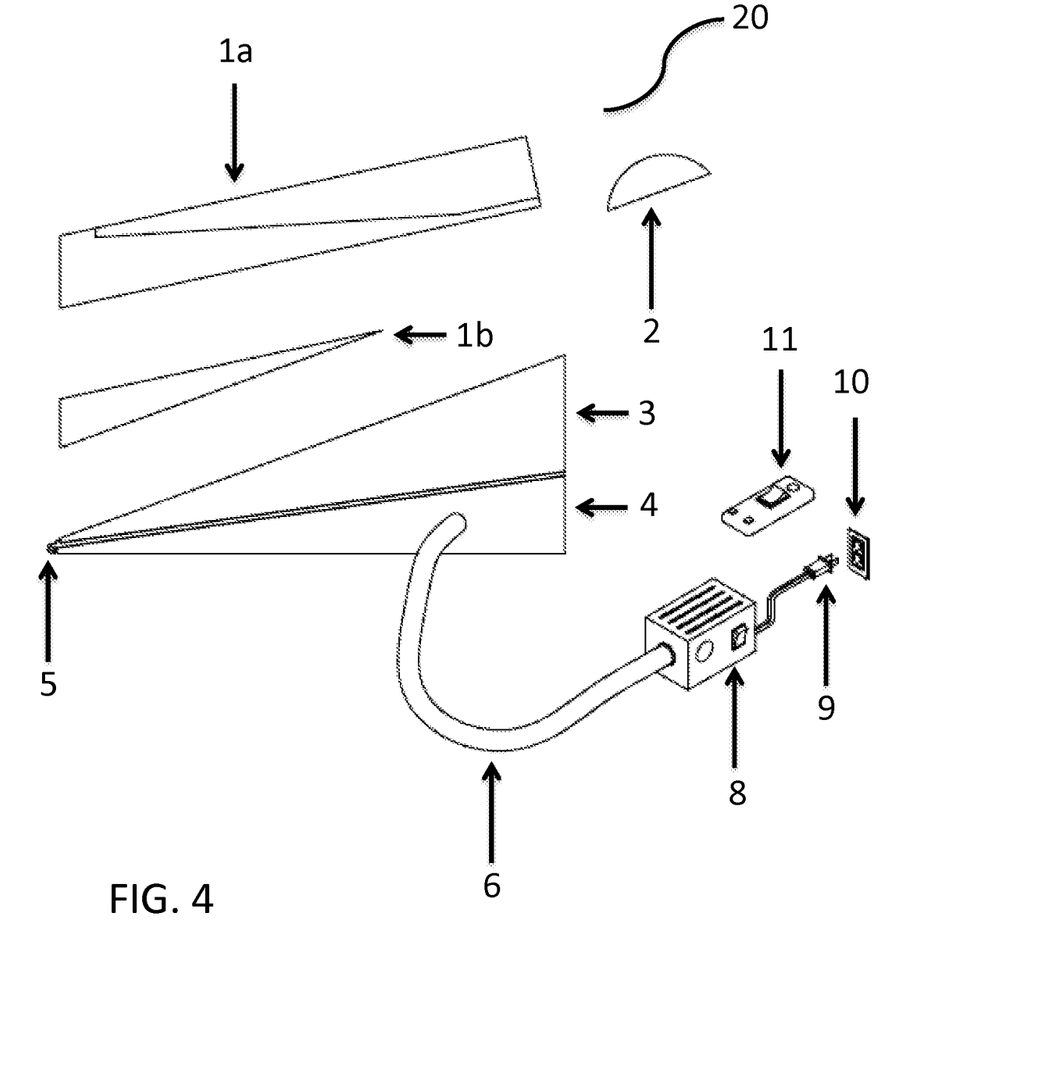
FIG. 4 is an exploded perspective view from the side of the exemplary embodiment of the invention.

FIG. 4 is an exploded side view of the exemplary embodiment of the bed wedge 20 showing the parts of the shoulder support wedge structure 1 which is composed of a top substantially rectangular shaped structure 1a and a bottom triangle shaped structure 1b. The bottom surface of structure 1a is detachably attached to the top surface of structure 1b through a hook and loop arrangement and placed on one side of the mattress 3 structure surface and attached to the mattress 3 structure surface through the underside of the bottom triangle shaped structure 1b by means of a hook and loop arrangement. This makes it possible for the shoulder support wedge structure 1 to be taken apart and lifted off the bed wedge 20 when not in use by a post shoulder surgery patient. The bed wedge 20 can also be used by a non-shoulder surgery person to rest, relax, read a book etc. on the bed by removing the shoulder support wedge structure 1 section from the mattress 3. In an alternative embodiment of the bed wedge 20 the bottom triangle shaped structure 1b would be provided in varying heights and angles depending upon the size of the patient to ensure the proper angle for post surgical shoulder recovery. For instance, the size of the bottom triangle shaped structure 1b would vary depending on whether the patient was a child or an adult. The bed wedge 20 pillow 2 is also held in place on the top end of the bed wedge 20 mattress 3 by means of a hook and loop arrangement. Having the shoulder support wedge structure 1 comprised of a top structure 1a and a bottom structure 1b held together by means of a hook and loop arrangement and the ability to remove pillow 2 from the mattress 3 makes it easy to disassemble and assemble bed wedge 20 as well as store it in a compact space when not needed.

Figure 5:
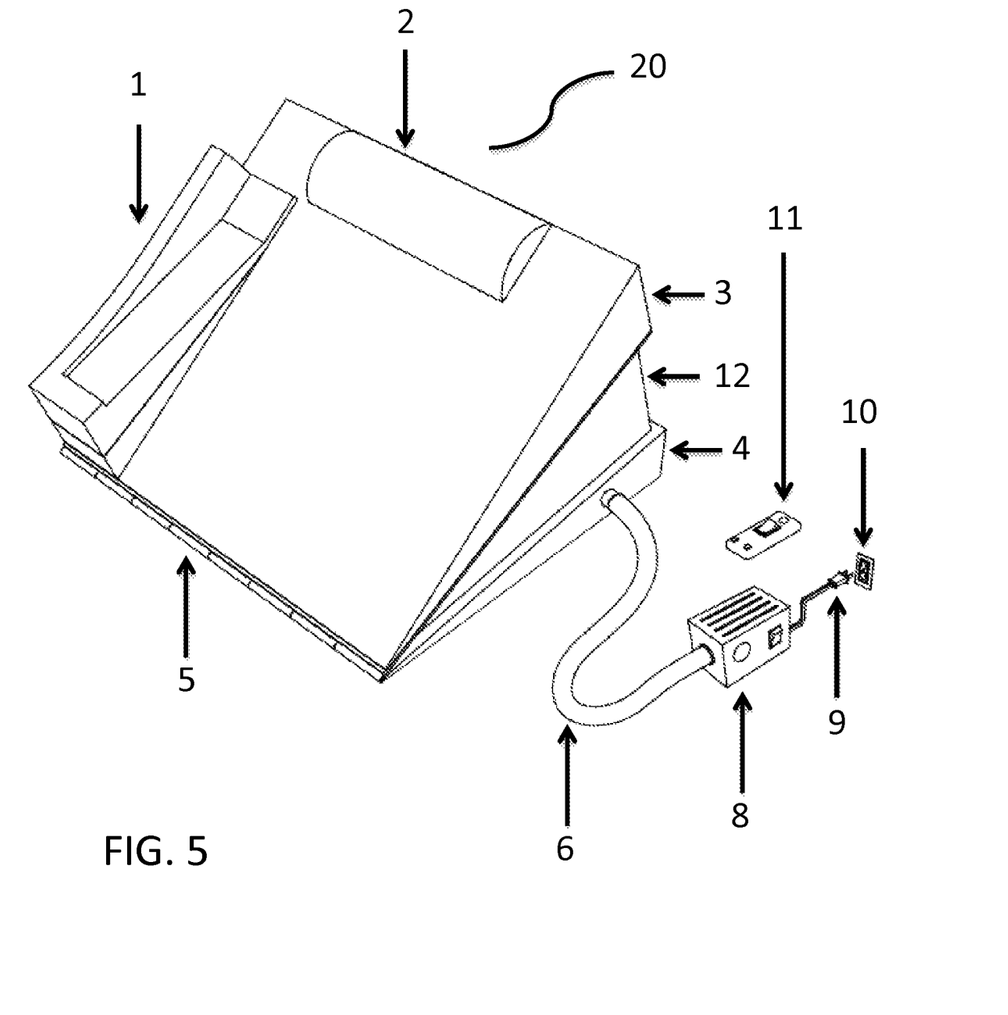
FIG. 5 is a perspective view of the exemplary embodiment of the present invention revealing the inflated inner core of the bed wedge.

FIG. 5 is a perspective view of the exemplary embodiment of the bed wedge 20 illustrating the inflated position of the inner core layer 12 of the bed wedge 20. The inner core layer 12 is layered between the upper mattress 3 structure and the lower solid frame 4 of the bed wedge 20. The inner core layer 12 is constructed of a flexible and collapsible material that is sturdy so that it can withstand the frequent inflation and deflation of the bed wedge 20 to different heights by the patient in an attempt to achieve the optimal comfort and support for the post surgical shoulder. In this embodiment, hinge 5 ensures that the inner core layer 12 inflates and deflates evenly throughout the length and width of the bed wedge 20 so as to avoid stress on the surgically repaired shoulder. In this embodiment of the bed wedge 20 when the patient wants to raise or lower the mattress 3 including the shoulder support wedge structure 1 in order to achieve the optimal comfort and support for the post surgical shoulder, they can easily reach out with their unencumbered hand to turn on the remote switch 11 to start the process of inflating or deflating the inner core 12 of the bed wedge 20. FIG. 5 along with FIGS. 1 and 2 and subsequent figures also illustrate the configuration of the shoulder support wedge structure 1 when the top substantially rectangular shaped structure 1a and the bottom triangle shaped structure 1b of the shoulder support wedge structure 1 are held together through a hook and loop arrangement to form the shoulder support wedge structure 1. As seen in these figures, the top substantially rectangular shaped structure 1a is configured with a triangular shaped slope within the rectangular shaped structure 1a with the narrow end of the triangular shaped slope forming the top end of the structure 1a where the postsurgical shoulder of a patient is held with the elbow of the patient held within the broad bottom end of the triangular shaped slope of structure 1a.

Figure 6:
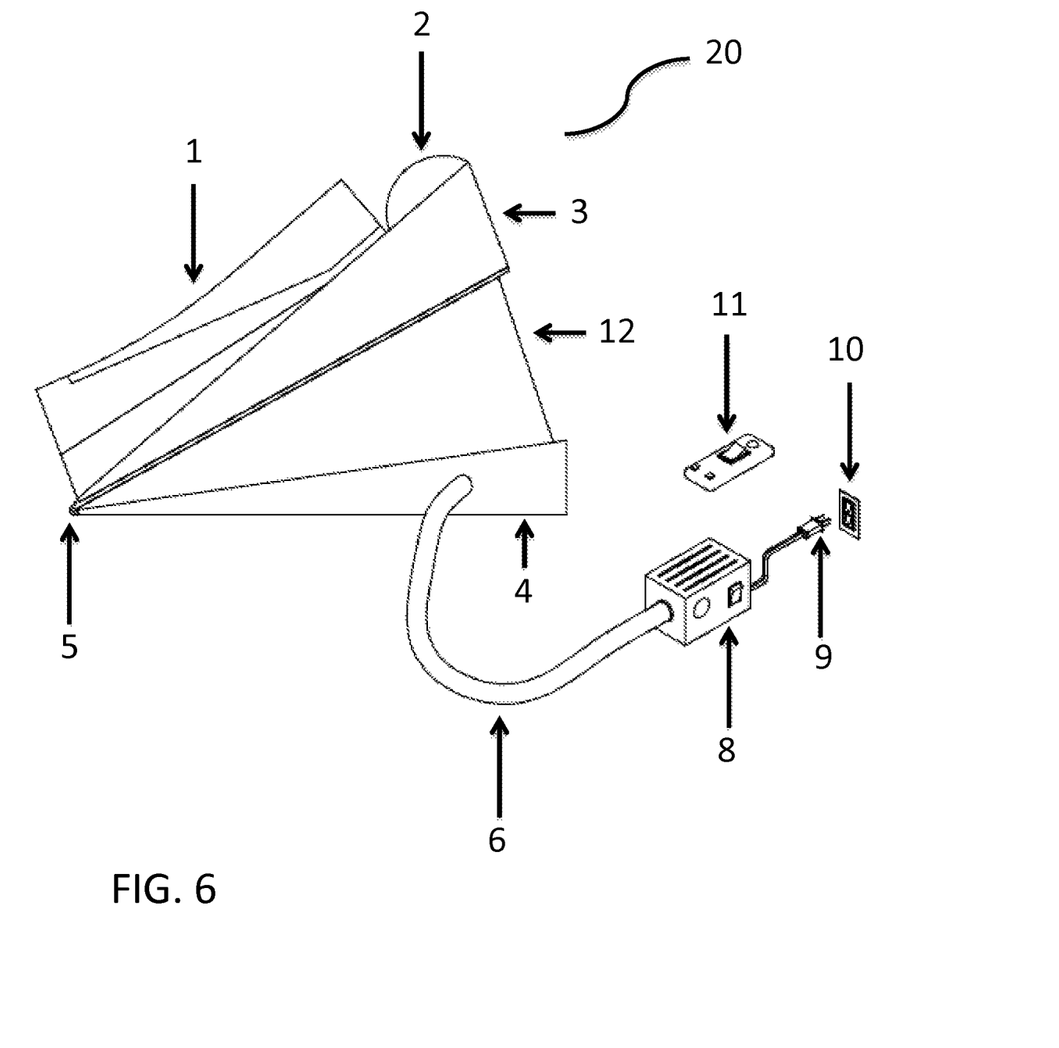
FIG. 6 is a side elevation view of the exemplary embodiment of the present invention with the inner core inflated.

FIG. 6 is a side perspective view of the inflated bed wedge 20 showing the inner core layer 12 inflated to its maximum potential providing approximately a 70° incline or more sufficient to lift the patient to a near full seated position when they want to sit up, get out of bed or have a drink or meal while in bed. In this embodiment, even with the patient in a fully seated position, the shoulder support wedge structure 1 firmly holds the post surgical shoulder in a sling or outside a sling at an angle that is comfortable to the patient.

Figure 7:
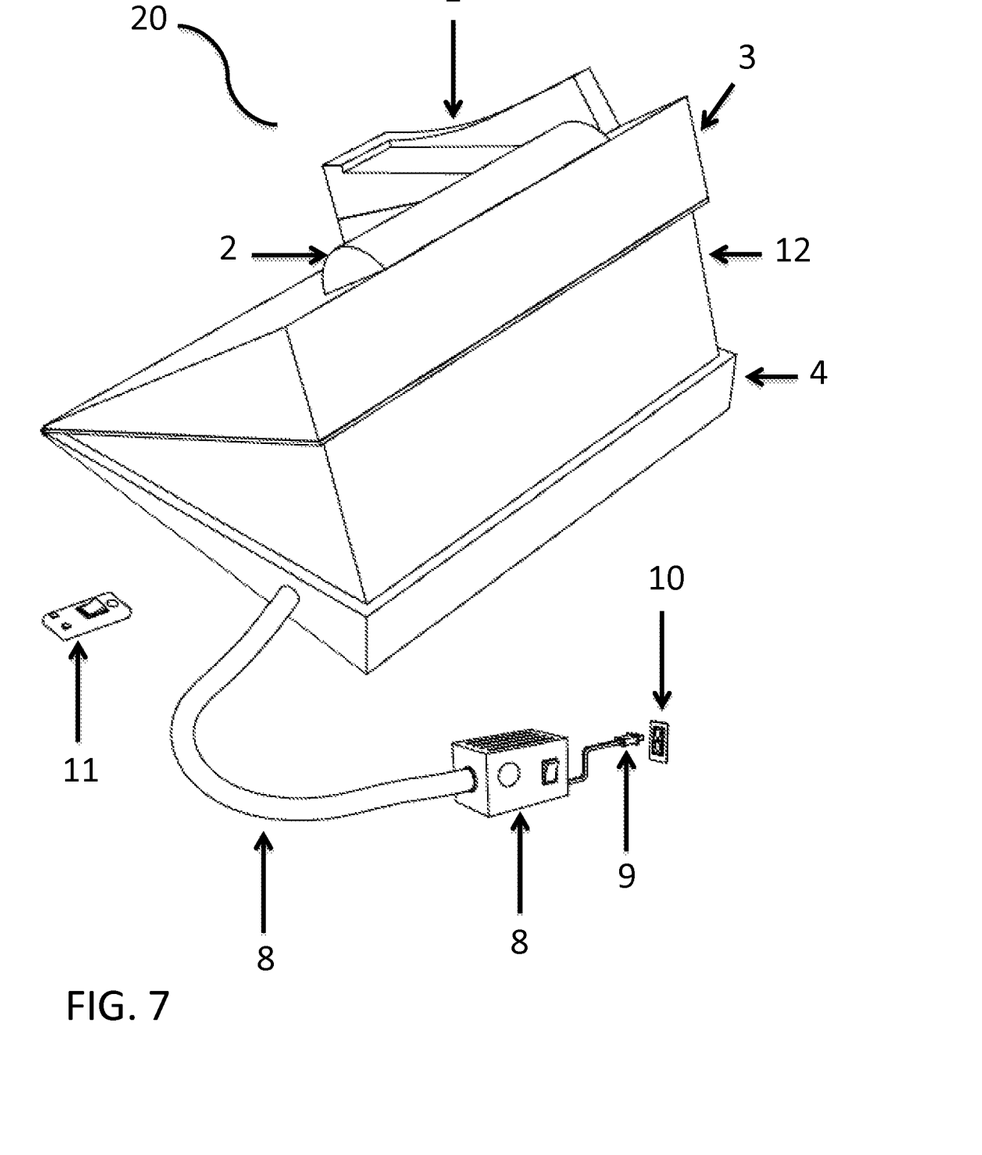
FIG. 7 is another perspective view from the back of the inflated bed wedge.

FIG. 7 is a perspective view from the back of the exemplary embodiment of the bed wedge 20 of the present invention highlighting the inflated inner core 12 lying between the upper mattress 3 structure and the lower solid frame 4 and illustrating the positioning of the shoulder support wedge structure 1 and the pillow 2 as they are viewed from the back of the bed wedge 20.

Figure 8:
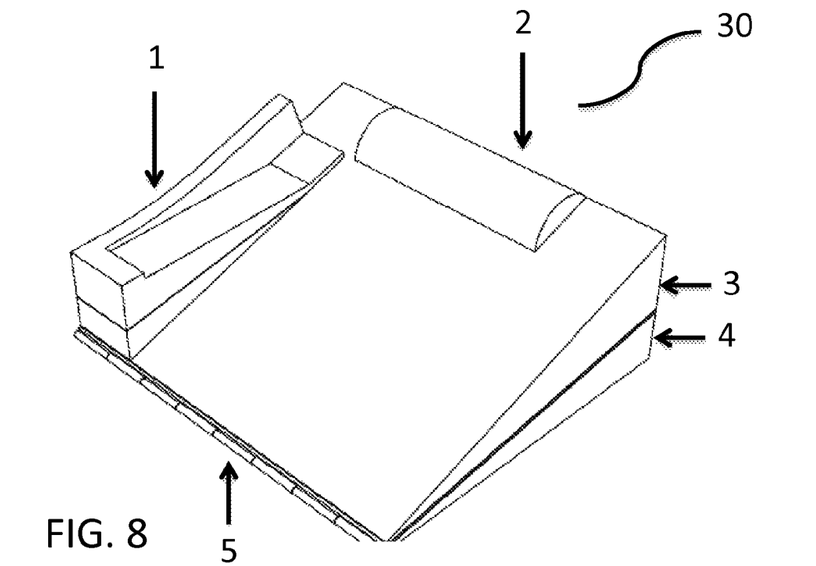
FIG. 8 and FIG. 9 are perspective views of an alternate embodiment of the bed wedge of the present invention.
Figure 9:
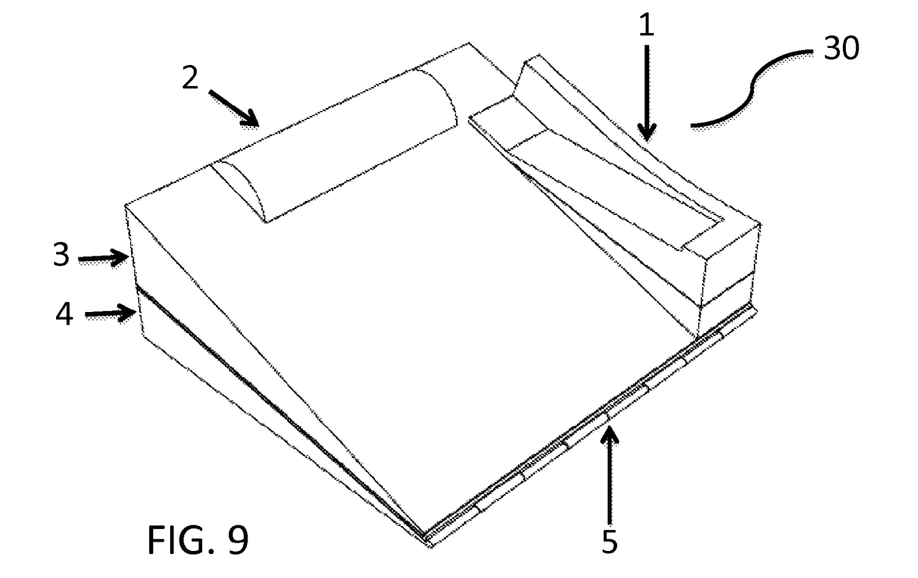

FIG. 8 and FIG. 9 are perspective views of an alternate embodiment of the present invention. In this embodiment, bed wedge 30 has all the features of the exemplary embodiment of the bed wedge 20 including the shoulder support wedge structure 1 detachable pillow 2 the upper mattress 3 the lower solid frame 4 and the hinge 5 connecting the mattress 3 with the solid frame 4 at their narrow ends. In this embodiment of the bed wedge 30 there is no inner core layer 12 or inflatable tubing attached to the solid frame 4 connecting the bed wedge 30 to an electromechanical inflation device or switch. Therefore, this alternate embodiment, bed wedge 30 is for use by post shoulder surgery patients who do not require the bed wedge to be raised or lowered while resting or sleeping in bed and maybe a cheaper alternative to the exemplary embodiment, bed wedge 20.

Figure 10:
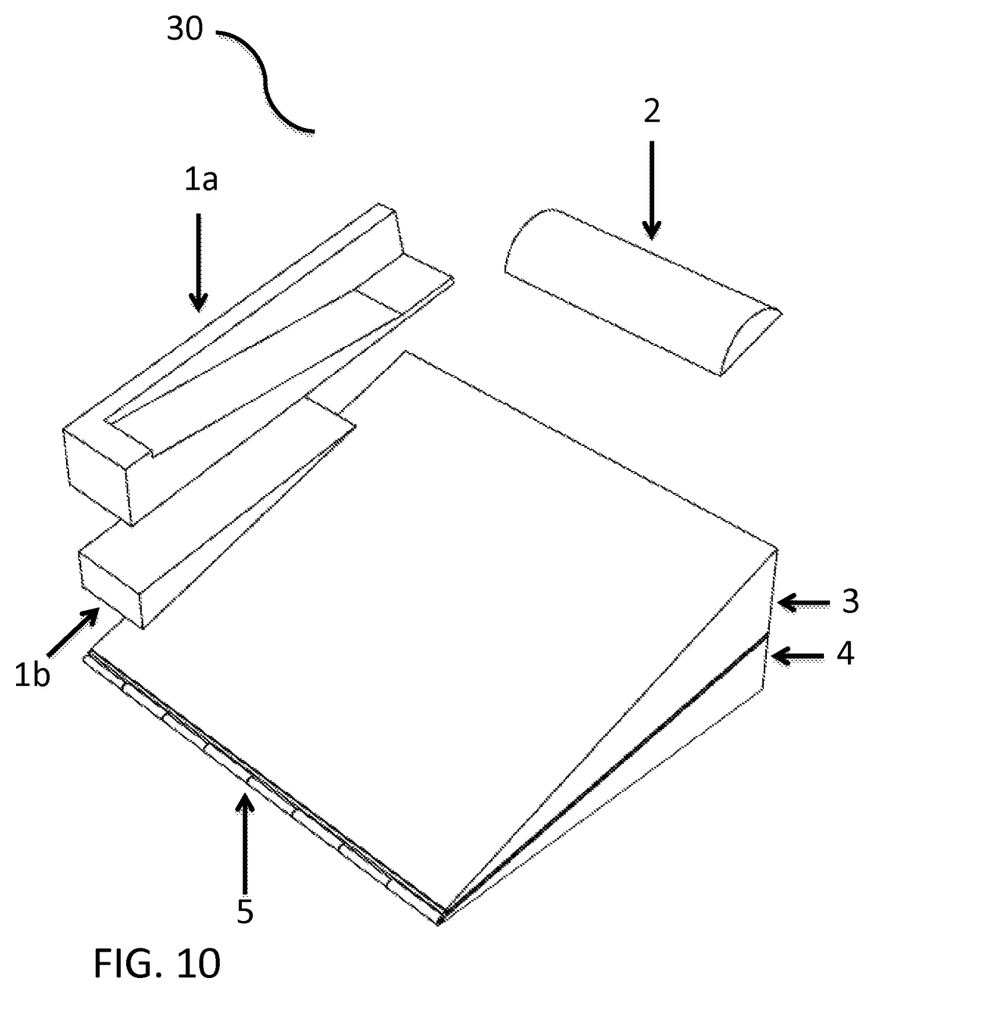
FIG. 10 is a perspective view of the use of the bed wedge by a post shoulder surgery patient.

FIG. 10 is an exploded view of the alternate embodiment 30 of the bed wedge 20 showing the shoulder support wedge structure 1 comprising the top substantially rectangular shaped structure 1a configured with the downward triangular shaped slope within the rectangular shaped structure 1a with the narrow end of the triangular shaped slope forming the top end of the structure 1a where the postsurgical shoulder of a patient is held with the elbow of the patient held within the broad bottom end of the triangular shaped slope of structure 1a. The bottom triangle shaped structure 1b of the shoulder support wedge structure 1 seen in relief in this figure is attached to the top rectangular shaped structure 1b through a hook and loop arrangement. The detachable pillow 2 is also shown in relief and exemplifies the ease with which the bed wedge 30 can be assembled or taken apart for storage.

Figure 11:
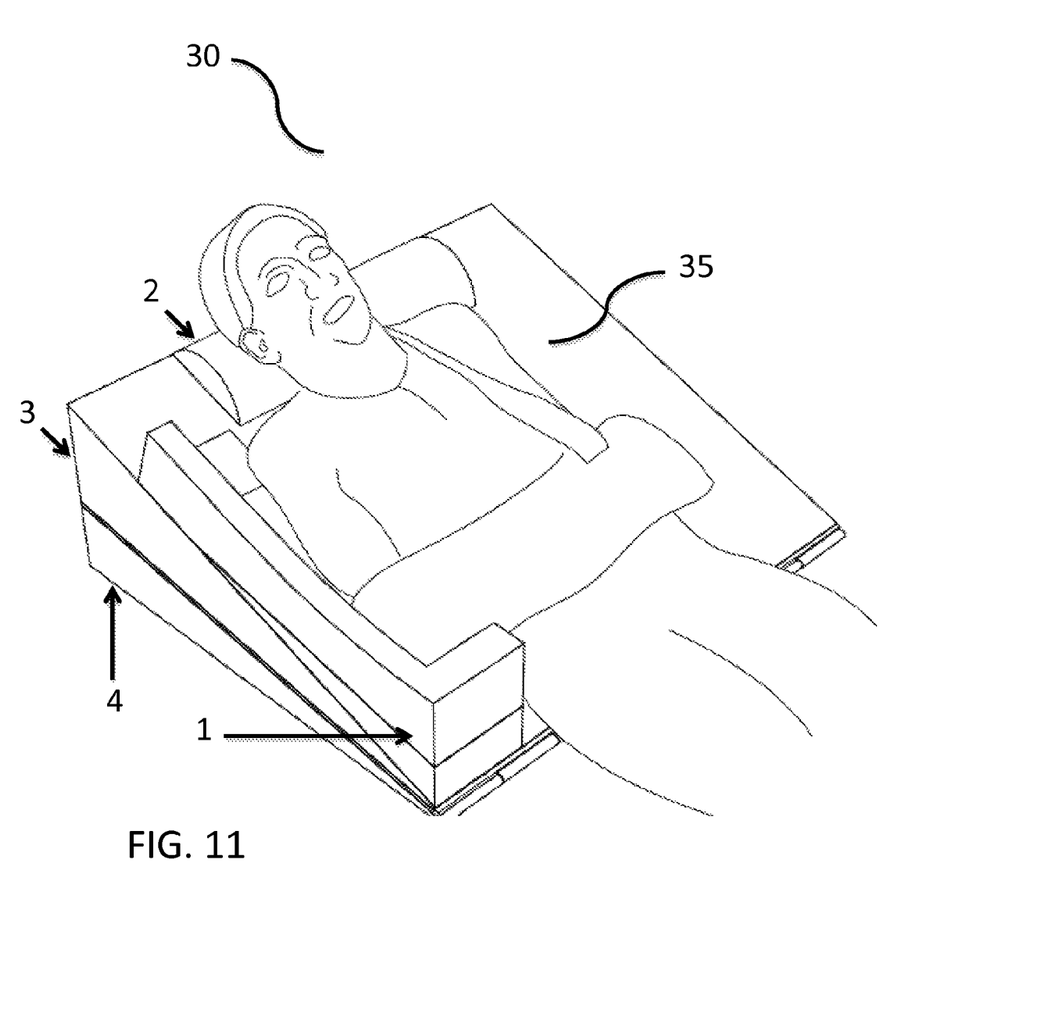
FIG. 11 is an exploded front view of the alternate embodiment of the bed wedge of the present invention.

FIG. 11 is a perspective view of the use of the bed wedge 20 or 30 by a post shoulder surgery patient. The figure illustrates the patient 35 reposing on the bed wedge 20 or 30 with his repaired shoulder in a surgical sling supported by the shoulder support wedge structure 1 and his head cradled on the pillow 2.

Figure 12:
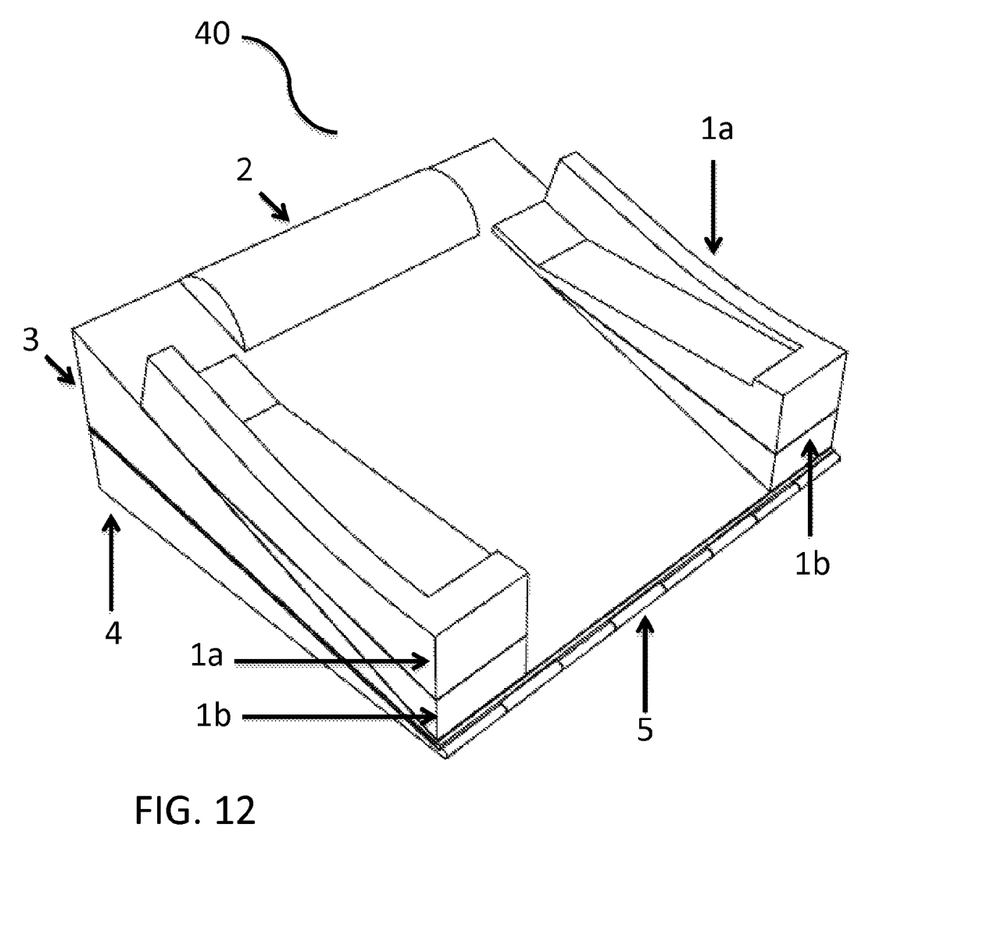
FIG. 12 is a perspective view of yet another embodiment of the bed wedge of the present invention.

FIG. 12 is yet another embodiment of the bed wedge of the present invention. In this embodiment, the bed wedge 40 is configured with two shoulder wedges one for the right side and the other for the left side of the bed wedge with identical shoulder support wedge structures 1 each comprising a top substantially rectangular structure 1a and a bottom triangle shaped structure 1b. The base structure of the bed wedge 40 with mattress 3 solid frame 4 detachable pillow 2 and hinge 5 are the same as in the exemplary embodiment bed wedge 20 and the alternate embodiment bed wedge 30.

Figure 13:
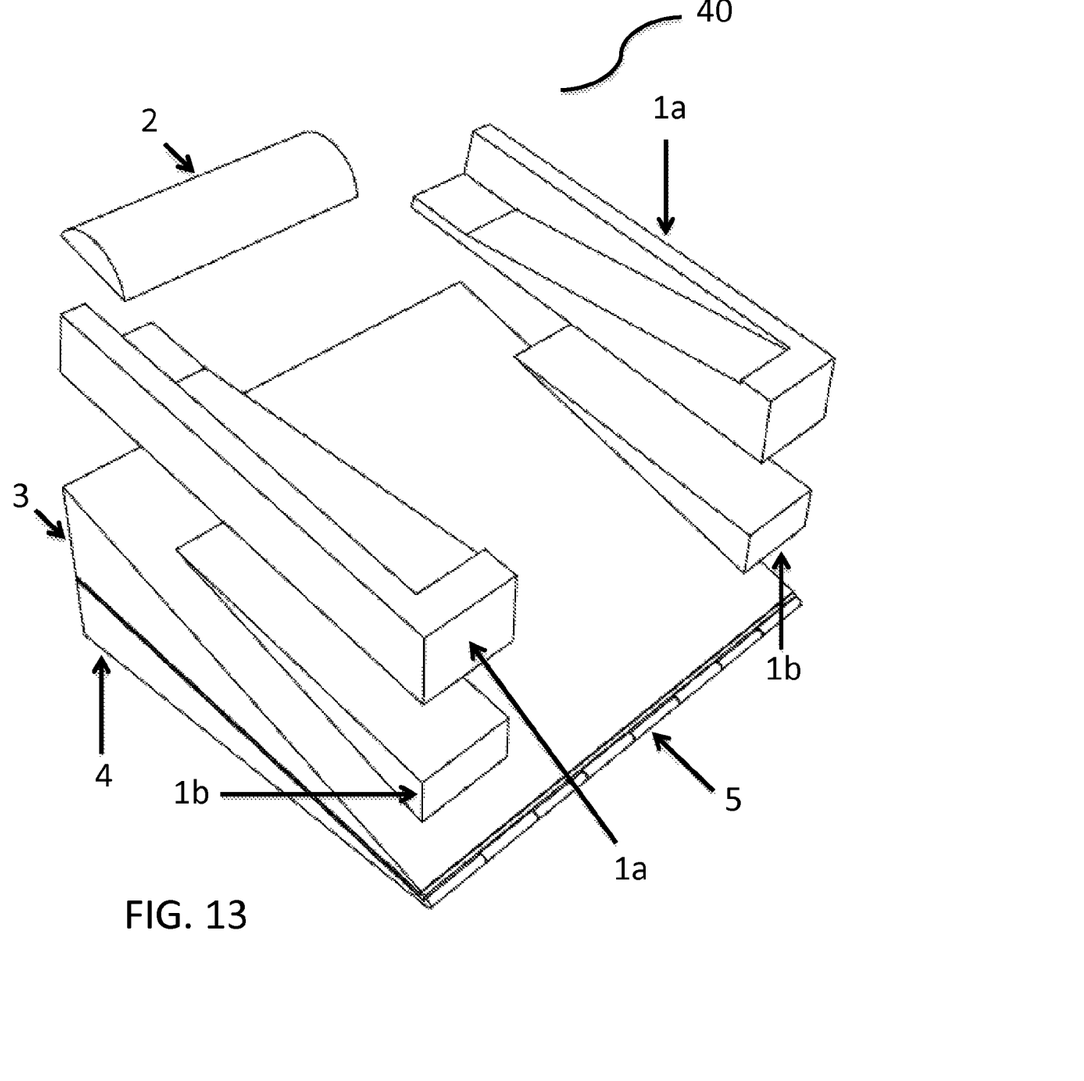
FIG. 13 is an exploded view of yet another embodiment of the bed wedge of the present invention.

FIG. 13 is an exploded view of the bed wedge 40 with the shoulder support wedge structures 1a and 1b and the detachable pillow 2 shown in relief off the base structure composed of the top mattress 3, the bottom solid frame 4 and the hinge 5 connecting the mattress 3 to the solid frame 4 at the front of the bed wedge 40.

The foregoing detailed description of the present invention through its figures and various embodiments should not be construed to limit the scope of the invention. It should be understood that the phraseology and terminology used to describe the invention are for descriptive purposes only and other phrase and terminology may be used to describe the relevant parts of the invention without departing from the scope of the invention. It should be further understood and obvious to those skilled in the art that alternatives, modifications and variations of the embodiments of the invention described herein are within the spirit and scope of the appended claims.

What is claimed is:

1. A portable post shoulder surgery rehabilitation shoulder support apparatus configured to support the shoulder of a post shoulder surgery patient, said apparatus comprising:
   a shoulder support structure member comprising a top rectangular shaped structure and a bottom triangle shaped structure;
   said top rectangular shaped structure configured with a triangle shaped slope within said rectangular shaped structure on one side of said rectangular shaped structure wherein a narrow end of said triangular shaped slope forms a top end of said shoulder support structure member to support a postsurgical shoulder of a patient and a broad bottom end of said triangular shaped slope configured to support an elbow of said patient;
   wherein a bottom surface of said top rectangular shaped structure of said shoulder support structure member is detachably attached to a top surface of said bottom triangle shaped structure of said shoulder support structure member by means of a hook and loop arrangement; and
   wherein said portable post shoulder surgery rehabilitation shoulder support apparatus comprising said shoulder support structure member having a top rectangular shaped structure and a bottom triangle shaped structure is placed on one side of a portable wedge-shaped mattress structure member by means of a hook and loop arrangement and said mattress structure member is further placed on a bed structure on which a post shoulder surgery patient supine's while recuperating from shoulder surgery.

2. The apparatus as described in claim 1 wherein said wedge-shaped mattress structure member has a wedge-shaped lower frame structure member and an inner core layer integrated between the two said structure members constructed of a flexible collapsible material that is capable of being inflated and deflated to a sufficient incline and angle using an electromechanical inflation device.

\* \* \* \* \*